United States Patent
Kim et al.

(10) Patent No.: US 6,486,098 B1
(45) Date of Patent: Nov. 26, 2002

(54) HERBICIDAL PHENOXYPROPIONIC ACID N-ALKYL-N-2-FLUOROPHENYL AMIDE COMPOUNDS

(75) Inventors: Dae Whang Kim; Hae Sung Chang; Young Kwan Ko; Jae Wook Ryu; Jae Chun Woo; Dong Wan Koo; Jin Seog Kim, all of Daejeon (KR)

(73) Assignee: Dongbu Hannong Chemical Co. Ltd., Seoul (KR)

( * ) Notice: Subject to any disclaimer, the term of this patent is extended or adjusted under 35 U.S.C. 154(b) by 0 days.

(21) Appl. No.: 09/744,450

(22) PCT Filed: Jul. 24, 1999

(86) PCT No.: PCT/KR99/00401

§ 371 (c)(1), (2), (4) Date: Feb. 20, 2001

(87) PCT Pub. No.: WO00/05956

PCT Pub. Date: Feb. 10, 2000

(30) Foreign Application Priority Data

Jul. 25, 1999 (KR) .............................. 98/30015

(51) Int. Cl.⁷ ..................... A01N 43/76; C07D 163/58
(52) U.S. Cl. ....................... 504/270; 548/221
(58) Field of Search ............... 504/270; 548/221

(56) References Cited

U.S. PATENT DOCUMENTS

| | | |
|---|---|---|
| 4,130,413 A | 12/1978 | Handte et al. |
| 4,531,969 A | 7/1985 | Nestler et al. |
| 4,554,014 A * | 11/1985 | Carter et al. .................. 71/94 |
| 4,640,703 A * | 2/1987 | Bohner et al. .................. 71/92 |
| 5,254,527 A | 10/1993 | Nestler et al. |

FOREIGN PATENT DOCUMENTS

| | | |
|---|---|---|
| JP | 02-011580 | 1/1990 |
| JP | 02-017187 | 1/1990 |

* cited by examiner

*Primary Examiner*—T. A. Solola
*Assistant Examiner*—Joseph Murray
(74) *Attorney, Agent, or Firm*—Lowe Hauptman Gilman & Berner, LLP

(57) ABSTRACT

(1)

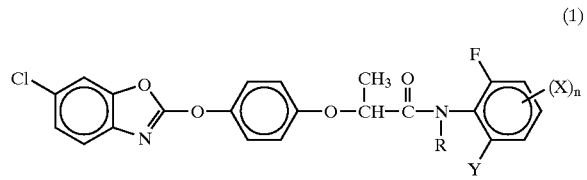

The present invention relates to novel herbicidal phenoxypropionic acid N-alkyl-N-2-fluorophenyl amides represented in formula (1), a method for preparing thereof, their use to control barnyard grass produced from rice and composition as suitable herbicides. In said formula, R is methyl or ethyl group; X is hydrogen, halogen, cyano, $C_1$~$C_6$ alkyl, $C_1$~$C_6$ alkoxy, $C_1$~$C_3$ haloalkyl substituted with 1 to 3 of halogen atom(s), $C_1$~$C_3$ haloalkoxy substituted with 1 to 3 of halogen atom(s), $C_2$~$C_4$ alkoxyalkoxy, phenoxy, benzyloxy, $C_2$~$C_6$ alkenyl, $C_2$~$C_6$ alkinyl, $C_2$~$C_6$ alkkenyloxy, $C_2$~$C_6$ alkinyloxy, or phenyl group; Y is hydrogen or fluoro; n is an integer of 1 or 2 and when n is 2, X can be in a combination of other substituents.

17 Claims, No Drawings

HERBICIDAL PHENOXYPROPIONIC ACID N-ALKYL-N-2-FLUOROPHENYL AMIDE COMPOUNDS

BACKGROUND OF THE INVENTION

1. Field of the Invention

The present invention relates to novel herbicidal phenoxypropionic acid N-alkyl-N-2-fluorophenyl amide compounds represented in the following formula (1), a method for preparing thereof, their use to control barnyard grass produced from rice and composition as suitable herbicides.

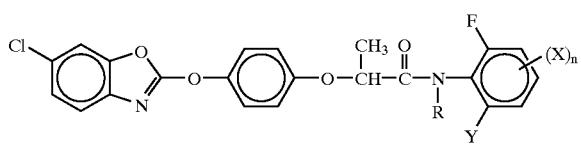

(1)

wherein,

R is methyl or ethyl group;

X is hydrogen, halogen, cyano, $C_1 \sim C_6$ alkyl, $C_1 \sim C_6$ alkoxy, $C_1 \sim C_3$ haloalkyl substituted with 1 to 3 of halogen atom(s), $C_1 \sim C_3$ haloalkoxy substituted with 1 to 3 of halogen atom(s), $C_2 \sim C_4$ alkoxyalkoxy, phenoxy, benzyloxy, $C_2 \sim C_6$ alkenyl, $C_2 \sim C_6$ alkinyl, $C_2 \sim C_6$ alkenyloxy, $C_2 \sim C_6$ alkinyloxy, or phenyl group;

Y is hydrogen or fluoro;

n is an integer of 1 or 2 and when n is 2, X can be in a combination of other substituents.

2. Description of the Prior Art

U.S. Pat. No. 4,130,413 discloses the compound containing the following formula (2).

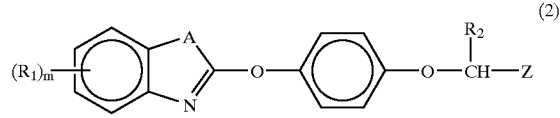

(2)

wherein, $(R_1)_m$ is hydrogen, halogen, $CF_3$, $NO_2$, CN or alkyl group; A is O, S or NH; $R_2$ is hydrogen or alkyl group; Z is

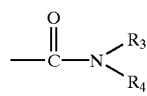

where $R_3$ and $R_4$, that are the same or different, are hydrogen, $C_1 \sim C_6$ alkyl, $C_3 \sim C_6$ hydroxyalkyl, $C_3 \sim C_6$ cycloalkyl, $C_1 \sim C_4$ alkoxy, or phenyl substituted where 1 to 3 substituents are selected from $C_1 \sim C_4$ alkyl group, $C_1 \sim C_6$ alkoxy group, halogen and $CF_3$ U.S. Pat. No. 4,531,969 discloses the compounds containing the following formula (3).

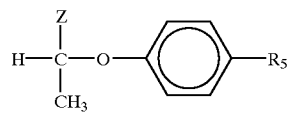

(3)

wherein, $R_5$ is

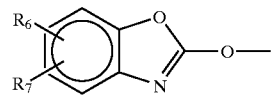

where $R_6$ is hydrogen or halogen atom, $R_7$ is hydrogen or alkyl group); Z is the same as defined above.

U.S. Pat. No. 5,254,527 discloses the compounds containing the following formula (4).

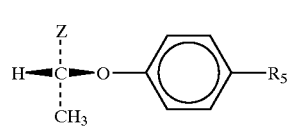

(4)

wherein, $R_5$ and Z are the same as defined above.

None of the patents teaches the synthesis of the compound represented in the above formula (1) and have tested the same for herbicidal activity.

JP Patent publication 2-11580 discloses the compound represented in the following formula (5).

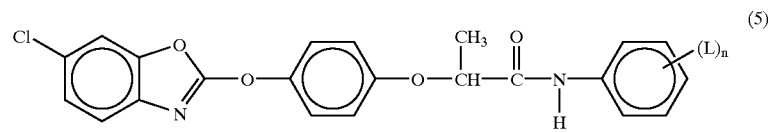

(5)

wherein, L is lower alkyl, halogen, methoxy, methoxyphenoxy, methylthio or methylvinyl group; n is an integer of 0 to 2.

JP Patent publication sho 53-40767 and sho 54-112828 also disclose that phenoxypropionic acid amide derivatives have herbicidal activity.

However, none of reports including the patents mentioned above has taught a method for preparing the compounds in the above formula (1) and tested the same against herbicidal activity. And also it has not been reported that the compounds have superior herbicidal activity and selectivity toward rice and control barnyard grass produced from rice.

SUMMARY OF THE INVENTION

Even though many of herbicides for rice have been recently developed and used, barnyard grass among weeds is the biggest problem in rice paddy.

Development of herbicides to control barnyard grass is an urgent to one who is in the field of agriculture. After transplanting young rice, herbicides, developed until now, cannot effectively control the production of barnyard grass so that it causes a huge damage to harvest. It has been reported that when barnyard grass is produced for one week in 1 $m^2$, amount of harvest decreases by 2%, for 5 weeks by about 10%, for 10 weeks by 19% and for 20 weeks by 35%.

Many herbicides have been used for the purpose of controlling barnyard grass that damages in amount of harvest of rice. However, the herbicide with a broader herbicidal activity, environmentally-friendly property and cost-effectiveness is still in demand.

The inventors have intensively studied to prepare herbicides to effectively control barnyard grass. As a result, they completed this invention to find a novel phenoxypropionic acid N-alkyl-N-2-fluorophenyl amide and its derivatives that are stable to rice and selectively control barnyard grass. This superior effectiveness is distinguished from the conventional inventions.

DETAILED DESCRIPTION OF THE INVENTION

The present invention is characterized by novel phenoxypropionic acid N-alkyl-N-2-fluorophenyl amide represented in the following formula (1) with an excellent herbicidal activity as well as selectively stable toward rice.

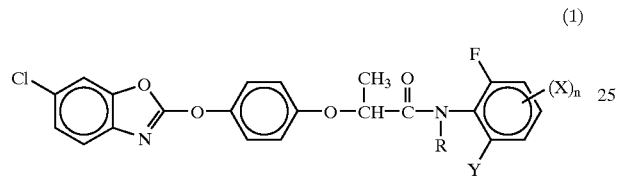

(1)

wherein, R, X, Y and n are the same as previously defined.

The compounds of the formula (1) according to the present invention may be specified as the following Table 1.

TABLE 1

(1)

| R | Y | X |
|---|---|---|
| CH$_3$ | H | H |
| CH$_2$CH$_3$ | H | H |
| CH$_3$ | H | 4-CN |
| CH$_3$ | H | 4-F |
| CH$_3$ | H | 3-F |
| CH$_3$ | H | 5-F |
| CH$_3$ | H | 4-Cl |
| CH$_3$ | H | 4,5-F$_2$ |
| CH$_3$ | H | 4-Br |
| CH$_3$ | H | 4-phenyl |
| CH$_3$ | H | 4-CH$_3$ |
| CH$_3$ | H | 3-Br |
| CH$_3$ | H | 4-CH$_2$CH$_3$ |
| CH$_3$ | H | 4-propyl |
| CH$_3$ | H | 4-isopropyl |
| CH$_3$ | H | 4-cyclopropyl |
| CH$_3$ | H | 4-butyl |
| CH$_3$ | H | 4-isobutyl |
| CH$_3$ | H | 3-CN |
| CH$_3$ | H | 4-OCH$_3$ |
| CH$_3$ | H | 4-O-phenyl |
| CH$_3$ | H | 4-OEt |
| CH$_3$ | H | 4-O-isopropyl |
| CH$_3$ | H | 4-O-allyl |
| CH$_3$ | H | 4-O-propyl |
| CH$_3$ | F | H |
| CH$_3$ | F | 3-F |
| CH$_3$ | F | 4-F |

TABLE 1-continued (1)

| R | Y | X |
|---|---|---|
| CH$_2$CH$_3$ | F | 4-F |
| CH$_3$ | F | 4-Cl |
| CH$_3$ | F | 4-Br |
| CH$_3$ | F | 4-CH$_3$ |
| CH$_3$ | F | 4-CH$_2$CH$_3$ |
| CH$_3$ | F | 4-propyl |
| CH$_3$ | F | 4-isopropyl |
| CH$_3$ | F | 4-cyclopropyl |
| CH$_3$ | F | 4-butyl |
| CH$_3$ | F | 4-isobutyl |
| CH$_3$ | F | 4-OCH$_3$ |
| CH$_3$ | F | 4-OEt |
| CH$_3$ | F | 4-O-isopropyl |
| CH$_3$ | F | 4-O-propyl |
| CH$_3$ | H | 3,5-F$_2$ |
| CH$_3$ | H | 5-F |
| CH$_3$ | H | 5-Cl |
| CH$_3$ | H | 5-Br |
| CH$_3$ | H | 5-CN |
| CH$_3$ | H | 5-CH$_3$ |
| CH$_3$ | H | 5-CH$_2$CH$_3$ |
| CH$_3$ | H | 5-phenyl |
| CH$_3$ | H | 5-propyl |
| CH$_3$ | H | 5-isopropyl |
| CH$_3$ | H | 5-cyclopropyl |
| CH$_3$ | H | 5-butyl |
| CH$_3$ | H | 5-isobutyl |
| CH$_3$ | H | 5-OCH$_3$ |
| CH$_3$ | H | 5-OEt |
| CH$_3$ | H | 5-O-isopropyl |
| CH$_3$ | H | 5-O-propyl |
| CH$_3$ | H | 5-O-phenyl |
| CH$_3$ | H | 5-O-allyl |
| CH$_3$ | F | 5-H |
| CH$_3$ | F | 5-F |
| CH$_3$ | F | 5-Cl |
| CH$_3$ | F | 5-Br |
| CH$_3$ | F | 5-CH$_3$ |
| CH$_3$ | F | 5-CH$_2$CH$_3$ |
| CH$_3$ | F | 5-propyl |
| CH$_3$ | F | 5-isopropyl |
| CH$_3$ | F | 5-cyclopropyl |
| CH$_3$ | F | 5-n-butyl |
| CH$_3$ | F | 5-isobutyl |
| CH$_3$ | F | 5-OCH$_3$ |
| CH$_3$ | F | 5-OEt |
| CH$_3$ | F | 5-O-isopropyl |
| CH$_3$ | F | 5-O-propyl |

The compounds of formula (1) according to this invention can be synthesized by a conventional method represented in the following scheme 1, reacting a compound of the formula (6) with a compound of the formula (7).

Scheme 1

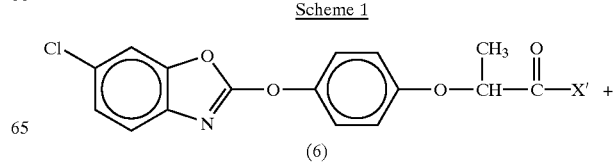

(6)

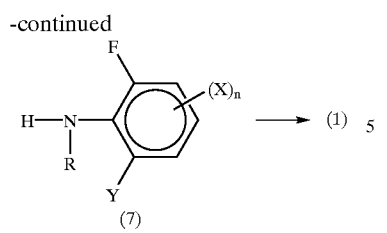

wherein, X' is OH, Cl, Br or phenoxy group; R, X, Y and n are the same as previously defined.

In the method according to scheme 1, it is prefer to use a binder such as triphenylphosphine and an organic base such as triethylamine or pyridine by keeping temperature at 0~100° C. in an inert solvent such as ethers like tetrahydrofuran, ethyethyl acetate, acetonitrile, toluene, xylene, hexane, methylene chloride, carbon tetrachloride, dichloroethane or the like, and to purify the crude product by column chromatography.

Another method for preparing the compounds (1) represented in the following scheme 2 is an alkylation of a compound of the formula (8) to compounds of the formula (9).

Scheme 2

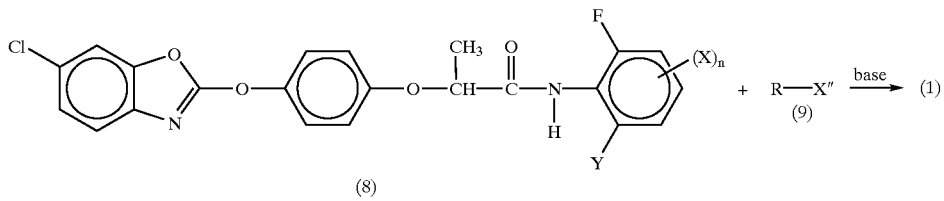

wherein, X", which is a leaving group, is Cl, Br, I, benzenesulfonyloxy, toluenesulfonyloxy, methanesulfonyloxy or lower alkyl sulfate group; R, X, Y and n are the same as previously defined.

In scheme 2, it is prefer to use a strong base which is enough to pull out a hydrogen from amide, NH. The strong base used in this invention is NaOH, KOH, LiOH, NaH, n-BuLi or LDA. It is prefer to carry this reaction at the temperature of −78~50° C. in an inert solvent such as ethers like ethylether, dioxane or tetrahydrofuran or hydrocarbons like hexane.

Another method for preparing the compounds (1) represented in the following scheme 3 is a reaction of a compound of the formula (10) with a compound of the formula (11) in the presence of a base.

Scheme 3

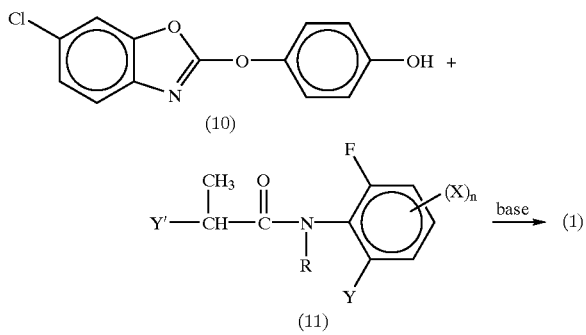

wherein, Y' is halogen, alkylsulfonyloxy, haloalkylsulfonyloxy, benzenesulfonyloxy or toluenesulfonyloxy group; R, X, Y, and n are the same as previously defined.

In Scheme 3, it is prefer to use inorganic bases such as alkali metal hydroxides like sodium hydroxide or potassium hydroxide, alkali metal carbonates like sodium carbonate or potassium carbonate, alkali metal hydrogencarbonates like sodium hydrogencarbonate or potassium hydrogencarbonate or organic bases like triethylamine, N,N-dimethylaniline, pyridine or 1,8-diazabicyclo[5,4,0]undec-7-ene.

A phase transition catalyst such as tetra-n-butylammonium bromide or 18-crown-6-[1,4,7,10,13,16-hexaoctacyclooctadecane] can be added to complete a reaction rapidly, if necessary. And also one or more than two solvents can be combined and used, if deemed necessary. It is prefer to use an inert organic solvent; for example; ketones such as acetone; aromatic hydrocarbons such as toluene, xylene or chlorobenzene; aliphatic hydrocarbons such as petroleum ether or ligroin; ethers such as diethylether, tetrahydrofuran or dioxane; nitrites such as acetonitrile or propionitrile; or amides such as N,N-dimethylformamide, N,N-dimethylacetamide, N-methylpyrrolidone. A reaction is carried at the temperature of from 0° C. to reflux, preferably 5~50° C. for 1 to 24 hour(s) to afford a high yield.

Another method for preparing the compound (1) represented in the following scheme 4 is a reaction of a compound of the formula (12) with a compound of the formula (13) in the presence of a base.

Scheme 4

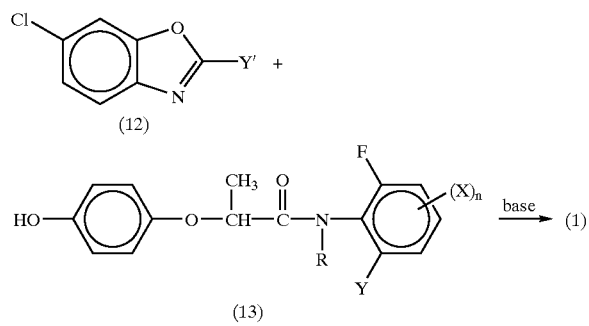

wherein, X, Y, Y', R and n are the same as previously defined.

In Scheme 4, it is prefer to use inorganic bases; for example; alkali metal hydroxides such as sodium hydroxide or potassium hydroxide, alkali metal carbonates such as sodium carbonate or potassium carbonate, alkali metal hydrogencarbonates such as sodium hydrogencarbonate or potassium hydrogencarbonate or organic bases such as triethylamine, N,N-dimethylaniline, pyridine, picoline, quinoline, or 1,8-diazabicyclo[5,4,0]undec-7-ene.

A phase transition catalyst such as tetra-n-butylammonium bromide or 18-crown-6[1,4,7,10,13,16-hexaoctacyclooctadecane] can be used, if necessary. And also one or more than two solvents can be combined and used if deemed necessary. It is prefer to use an inert organic solvent; for example; ketones such as acetone or butanone; aromatic hydrocarbons such as benzene, toluene, xylene or chlorobenzene; aliphatic hydrocarbons such as petroleum ether, or ligroin; ethers such as diethylether, tetrahydrofuran or dioxane; nitriles such as acetonitrile or propionitrile; or amides such as N,N-dimethylformamide, N,N-dimethyl acetamide or N-methylpyrrolidone. A reaction is carried at the temperature of from0° C. to reflux, preferably 20~100° C. for 1 to 24 hour(s) to afford a high yield.

The present invention is explained in more detail by the following examples but is not limited by these examples.

EXAMPLE 1

N-(2-Fluorophenyl)-N-methyl-2-bromo-propionamide

2-Bromopropionic acid(3.4 g, 0.022 mol) and 2-fluoroaniline(3 g, 0.024 mol) were dissolved in 50 ml of chloroform and cooled to 0° C. A solution of dicyclohexylcarbodiimide(5 g, 0.024 mol) in 10 ml of chloroform was slowly injected through a syringe. A temperature of the reaction mixture was raised to room temperature and it was stirred for 1 hour. Solid remained during the reaction was filtered out and washed twice with 20 ml of chloroform. The filtrate was concentrated under reduced pressure and the crude product was purified by column chromatography (eluent; ethyl acetate/n-hexane=1/3) to afford 5 g of the target product.

$^1$H-NMR(CDCl$_3$): δ 1.7(3H, d), 3.24(3H, s), 4.16(0.7H, q), 4.34(0.3H, q), 7.13~7.48(4H, m).

EXAMPLE 2

N-(2-Fluorophenyl)-N-methyl-2-(4-hydroxyphenoxy)propionamide

N-(2-fluorophenyl)-N-methyl-2-bromopropionamide (18.2 g, 0.07 mol), hydroquinone(7 g, 0.064 mol), potassium carbonate(10.54 g, 0.076 mol) and tetra-n-butylammonium bromide(1 g) were dissolved in 350 ml of acetonitrile and heated at reflux for 6 hours. The reaction mixture was cooled to room temperature and solid remained during the reaction was filtered out. The filtrate was concentrated under reduced pressure and the crude product was purified by column chromatography(eluent: ethyl acetate/n-hexane=1/2) to afford 16 g of the target product.

$^1$H-NMR(CDCl$_3$): δ 1.42(3H, t), 3.25(3H, s), 4.56(1H, q), 6.5–7.4(8H, m).

EXAMPLE 3

2-[4-(6-Chloro-2-benzoxazoyloxy)-phenoxy] propionic Acid-N-(2-fluorophenyl)-N-methylamide N-(2-fluorophenyl)-N-methyl-2-(4-hydroxyphenoxy) propionamide (11.5 g, 0.04 mol), 2,6-dichlorobenzoxazole (6.85 g, 0.036 mol), potassium carbonate (6 g, 0.043 mol) and tetra-n-butylammonium bromide (1 g) were dissolved in 300 ml of acetonitrile and heated at reflux for 7 hours. The reaction mixture was cooled to room temperature and solid remained during the reaction was filtered out. The filtrate was concentrated under reduced pressure and the crude product was purified by column chromatography (eluent: ethyl acetate/n-hexane=1/3) to afford 12.5 g of the target product.

$^1$H-NMR(CDCl$_3$): δ 1.42(3H, t), 3.3(3H, s), 4.62(1H, m), 6.8~7.4(1H, m).

EXAMPLE 4

2-[4-(6-Chloro-2-benzoxazoyloxy)-phenoxy] propionic Acid-N-(2-fluorophenyl)amide 2-[4-(6-chloro-2-benzoxazoyloxy)-phenoxy]propionic acid (346.7 mg, 1 mmol) was dissolved in 10 ml of tetrahydrofuran. 2-fluoroaniline(111.12 mg, 1 mmol), triphenylphosphine(393.4 mg, 1.5 mmol), triethylamine (0.15 ml, 1 mmol) and carbon tetrachloride(1 ml) were added sequentially and heated at reflux for 8 hours. The reaction mixture was cooled to room temperature and acidified with 5% hydrochloric acid, followed by addition of water. The acidified reaction mixture was extracted three times with ethyl acetate. The combined organic solvent layer was dried over magnesium sulfate, filtered and concentrated under reduced pressure. The crude product was purified by column chromatography(eluent: ethyl acetate/n-hexane=1/4) to afford 200 mg of the target product.

m.p: 132~136° C.; $^1$H-NMR(CDCl$_3$): δ 1.7(3H, d), 4.81 (1H, q), 7.05~7.45(10H, m), 8.35(1H, m), 8.5(1H, br).

EXAMPLE 5

2-[4-(6-Chloro-2-benzoxazoyloxy)-phenoxy] propionic Acid-N-(2-fluorophenyl)-N-methyl Amide 2-[4-(6-Chloro-2-benzoxazoyloxy)-phenoxy] propionic acid-N-(2-fluorophenyl)amide (100 mg, 0.24 mmol) was dissolved in 10 ml of anhydrous tetrahydrofuran and 60% NaH(10 mg, 0.24 mmol) and CH$_3$I(34 mg, 0.24 mmol) were added sequentially at 0° C. The reaction mixture was stirred at room temperature for 5 hours. Ice water was poured to the reaction mixture and it was extracted three times with ethyl acetate. The combined organic solvent layer was dried over magnesium sulfate, filtered and concentrated under reduced pressure. The crude product was purified by column chromatography(eluent: ethyl acetate/n-hexane=1/4) to afford 75 mg of the target product.

$^1$H-NMR(CDCl$_3$): δ 1.42(3H, t), 3.3(3H, s), 4.62(1H, m), 6.8 7.4(11H, m).

EXAMPLE 6

2-[4-(6-Chloro-2-benzoxazoyloxy)-phenoxy] propionic Acid-N-(2-fluorophenyl)-N-methyl Amide 2-[4-(6-Chloro-2-benzoxazoyloxy)-phenoxy]propionic acid(346.7 mg, 1 mmol) was dissolved in 10 ml of tetrahydrofuran and N-methyl-2-fluoroaniline(125 mg, 1 mmol), triphenylphosphine(393.4 mg, 1.5 mmol), triethylamine (0.15 ml, 1 mmol) and carbon tetrachloride(1 ml) were added sequentially and the reaction was heated at reflux for 12 hours. The reaction mixture was cooled to room temperature and acidified with 5% hydrochloric acid, followed by addition of water. The acidified reaction mixture was extracted three times with ethyl acetate. The combined organic solvent layer was dried over magnesium sulfate, filtered and concentrated under reduced pressure. The crude product was purified by column chromatography(eluent: ethyl acetate/n-hexane=1/2) to afford 100 mg of the target product.

EXAMPLE 7

2-[4-(6-Chloro-2-benzoxazoyloxy-phenoxy) propionic Acid-N-ethyl-N-(2-fluorophenyl)amide 2-[4-(6-chloro-2-benzoxazoyloxy)-phenoxy]-N-(2-fluorophenyl)propionamide (100 mg, 0.24 mmol) was dissolved in 10 ml of anhydrous tetrahydrofuran and 60% NaH(10 mg, 0.24 mmol) and bromoethane(27 mg, 0.24 mmol) were added sequentially at 0° C. and then the reaction mixture was stirred at room temperature for 8 hours. Ice water was poured to the reaction mixture and it was extracted three times with ethyl acetate. The combined organic solvent layer was dried over magnesium sulfate, filtered and concentrated under reduced pressure. The crude product was purified by column chromatography(eluent: ethyl acetate/n-hexane=1/2) to afford 60 mg of the target product.

¹H-NMR(CDCl₃): δ 1.1(3H, t), 1.42(3H, d), 3.8(2H, q), 4.62(1H, q), 6.7~7.4(11H, m).

EXAMPLE 8

2-[4-(6-Chloro-2-benzoxazoyloxy)-phenoxy] propionic Acid-N-methyl-N-(2,4,5-trifluoro phenyl) amide 2-[4-(6-chloro-2-benzoxazoyloxy)-phenoxy]propionic acid(0.693 g, 2 mmol) was dissolved in 15 ml of tetrahydrofuran and N-methyl-2,4,5-trifluoroaniline(0.322 g, 2 mmol), triphenylphosphine(0.78g, 2 mmol), triethylamine (0.4 ml) and carbon tetrachloride(2 ml) were added sequentially and then the reaction mixture was heated at reflux for 18 hours. The reaction mixture was cooled to room temperature and acidified with 5% hydrochloric acid. The acidified reaction mixture was extracted three times with ethyl acetate. The combined organic solvent layer was dried over magnesium sulfate, filtered and concentrated under reduced pressure. The crude product was purified by column chromatography(eluent: ethyl acetate/n-hexane=1/2) to afford 250 mg of the target product.

¹H-NMR(CDCl₃): δ 1.42(3H, d), 3.2(3H, s), 4.65(1H, m), 6.6~7.4(9H, m).

EXAMPLE 9

2-[4-(6-Chloro-2-benzoxazoyloxy)-phenoxy] propionic Acid-N-methyl-N-(2,6-difluoro-phenyl) amide 2-[4-(6-chloro-2-benzoxazoyloxy)-phenoxy]propionic acid(0.693 g, 2 mmol) and N-methyl-2,6-difluoroaniline (0.284 g, 2 mmol) were dissolved in 20 ml of tetrahydrofuran and triphenylphosphine(0.78 g, 2 mmol), triethylamine(0.42 ml) and carbon tetrachloride(2 ml) were added sequentially. The reaction mixture was heated at reflux for 16 hours. The reaction mixture was cooled to room temperature and acidified with 5% hydrochloric acid. The acidified reaction mixture was extracted three times with ethyl acetate. The combined organic solvent layer was dried over magnesium sulfate, filtered and concentrated under reduced pressure. The crude product was purified by column chromatography(eluent: ethyl acetate/n-hexane=1/2) to afford 205 mg of the target product.

¹H-NMR(CDCl₃): δ 1.4(3H, d), 3.3(3H, s), 4.62(1H, q), 6.8~7.4(10H, m).

EXAMPLE 10

2-[4-(6-Chloro-2-benzoxazoyloxy)-phenoxy] propionic Acid-N-(2,4-difluorophenyl)-N-methyl Amide 2-[4-(6-chloro-2-benzoxazoyloxy)-phenoxy]propionic acid(0.693 g, 2 mmol) was dissolved in 15 ml of tetrahydrofuran and N-methyl-2,4-difluoroaniline(0.284 g, 2 mmol), triphenylphosphine(0.78 g, 2 mmol), triethylamine (0.42 ml) and carbon tetrachloride(2 ml) were added sequentially. The reaction mixture was heated at reflux for 16 hours. The reaction mixture was cooled to room temperature and acidified with 5% hydrochloric acid, followed by addition of water. The acidified reaction mixture was extracted three times with ethyl acetate. The combined organic solvent layer was dried over magnesium sulfate, filtered and concentrated under reduced pressure. The crude product was purified by column chromatography(eluent: ethyl acetate/n-hexane=1/2) to afford 230 mg of the target product.

¹H-NMR(CDCl₃): δ 1.4(3H, d), 3.2(3H, s), 4.6(1H, q), 6.6~7.2(10H, m).

EXAMPLE 11

2-[4-(6-Chloro-2-benzoxazoyloxy)-phenoxy] propionic Acid-N-methyl-N-(2,3,6-trifluorophenyl) amide 2-[4-(6-chloro-2-benzoxazoyloxy)-phenoxy]propionic acid(0.693g, 2 mmol) was added to 6 ml of thionyl chloride and the reaction mixture was heated at reflux for 2 hours. Excess of thionyl chloride was removed under reduced pressure and 3 ml of anhydrous tetrahydrofuran was added to it. A solution of N-methyl-2,3,6-trifluoroaniline(0.32 g, 2 mmol) and triethyl amine(0.42 ml) in anhydrous tetrahydrofuran(10 ml) was added slowly to the reaction mixture at 0° C. The mixture was stirred at 0° C. for 30 minutes and stirred at room temperature for additional 1 hour. After pouring water the reaction mixture was extracted three times with ethyl acetate. The combined organic solvent layer was dried over magnesium sulfate, filtered and concentrated under reduced pressure. The crude product was purified by column chromatography(eluent: ethyl acetate/n-hexane=1/2) to afford 240 mg of the target product.

¹H-NMR(CDCl₃): δ 1.45(3H, d), 3.25(3H, s), 4.6(1H, q), 6.7~7.4(9H, m).

EXAMPLE 12~17

The compounds represented in the following Table 2 were prepared by the same procedure of example 11 except using of aniline compounds instead of N-methyl-2,3,6-trifluoroaniline.

TABLE 2

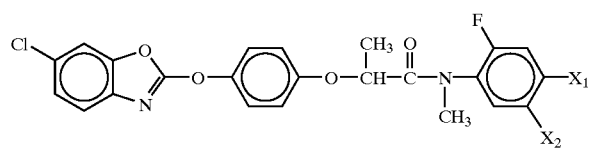

| Example | X₁ | X₂ | ¹H-NMR(CDCl₃) |
|---|---|---|---|
| Exam. 12 | H | CH₃ | 1.42(3H, t), 2.3(3H, s), 3.25(3H, s), 4.62(1H, m), 6.8~7.4(10H, m) |
| Exam. 13 | Cl | H | 1.42(3H, t), 3.3(3H, s), 4.62(1H, m), 6.7~7.5(10H, m) |

TABLE 2-continued

[Chemical structure: Chlorobenzoxazole-O-phenyl-O-CH(CH₃)-C(O)-N(CH₃)-fluorophenyl with X₁, X₂ substituents]

| Example | X₁ | X₂ | ¹H-NMR(CDCl₃) |
|---|---|---|---|
| Exam. 14 | H | F | 1.42(3H, t), 3.3(3H, s), 4.62(1H, m), 6.5~7.4(10H, m) |
| Exam. 15 | CH₃ | H | 1.42(3H, t), 2.38(3H, s), 3.25(3H, s), 4.62(1H, m), 6.8~7.4(10H, m) |
| Exam. 16 | OCH₃ | H | 1.42(3H, t), 3.25(3H, s), 3.8(3H, s), 4.65(1H, m), 6.65~7.45(10H, m) |
| Exam. 17 | OCH₂CH₃ | H | 1.25(3H, t), 1.42(3H, t), 3.25(3H, s), 4.0(2H, q), 4.62(1H, m), 6.65~7.42(10H, m) |

Formulation

In order to use the compounds according to the present invention as herbicides, they should be formulated in such a suitable type such as wettable powder, emulsions, granules, dusts, suspensions and solutions by combining a carrier, a surfactant, a dispersing agent or a supplement agent. Many of these may be applied directly or after diluted with suitable media. Formulations can be prepared at spray volume of from hundreds liters to thousands liters per hectare. The formulations contain about 0.1% to 99% by weight of active ingredient(s) and 0.1% to 20% surfactant(s) or 0% to 99.9% solid or liquid diluent(s) are recommended to be added. The formulations will contain these ingredients in the following approximate proportions shown in Table 3.

TABLE 3

| | Weight Percent (%) | | |
|---|---|---|---|
| Formulations | Active ingredient | Diluent | Surfactant |
| Wettable powders | 10~90 | 0~74 | 1~10 |
| Suspension | 3~50 | 40~95 | 0~15 |
| Emulsions Solution | 3~50 | 40~95 | 0~15 |
| Granules | 0.1~95 | 5~99.9 | 1~15 |

The proportion of active ingredients is depending on the intended use. Higher ratios of a surfactant to active ingredients are sometimes desirable and are achieved by incorporation into the formulation or tank mixing.

Solid diluents with high absorption are preferred for wettable powders. Liquid diluents and solvents are preferably stable against phase separation at 0° C. All the formulations may contain a small amount of additives to prevent forming, caking, corrosion and growth of microorganisms.

According to conventional methods to prepare the composition, solutions can be made only by blending ingredients and fine solids by blending and pulverizing with hammer-mill. Suspensions can be made by wet-milling and granules can be made by spraying the active ingredients on performed granular carrier.

Preparation examples of typical formulations are as follows.

Formulation1: Wettable Powders

The ingredients are thoroughly blended, re-blended after spraying liquid surfactant on the solid ingredients and hammer-milled until all the solids are essentially under 100 μm.

| | |
|---|---|
| Active ingredient (Example 3 Compound) | 20 wt % |
| Dodecylphenol polyethylene glycol ether | 2 wt % |
| Sodium ligninsulfonate | 4 wt % |
| Sodium silicon aluminate | 6 wt % |
| Montmorillonite | 68 wt % |

Formulation 2: Wettable Powders

The ingredients are blended, hammer-milled until all the solids are under 25 μm and packaged.

| | |
|---|---|
| Active ingredient (Example 3 Compound) | 80 wt % |
| Sodium alkyl naphthalenesulfonate | 2 wt % |
| Sodium ligninsulfonate | 2 wt % |
| synthetic amorphous silica | 3 wt % |
| Kaolinite | 13 wt % |

Formulation 3: Emulsions

The ingredients are mixed and homogeneously dissolved to give emulsions.

| | |
|---|---|
| Active ingredient (Example 3 Compound) | 30 wt % |
| Cyclohexanone | 20 wt % |
| Polyoxyethylene alkylaryl ether | 11 wt % |
| Calcium alkylbenzenesulfonate | 4 wt % |
| Methylnaphthalene | 35 wt % |

Formulation 4: Granules

The ingredients were thoroughly blended. 20 Weight part of water was added to 100 weight part of the ingredient mixture. The ingredient mixture was granulated with a size of 14 to 32 mesh by using extrusive granulator and dried.

| | |
|---|---|
| Active ingredient (Example 3 Compound) | 5 wt % |
| Sodium laurylalcoholsulfonate | 2 wt % |
| Sodium ligninsulfonate | 5 wt % |
| Carboxymethyl cellulose | 2 wt % |
| Potassium sulfate | 16 wt % |
| Plaster | 70 wt % |

The formulations according to this invention were sprayed with diluting to a certain concentration.

Utility

The compounds according to the present invention represent high activity as leaf treatment herbicides for rice and especially effective in rice due to an excellent control of barnyard grass.

The active ingredients can be used from 10 g to 4 kg per hectare, preferably from 50 g to 400 g. The amount of the compounds of the present invention depends on the amount and size of weeds and formulations. The herbicides of the present invention can be used as alone or in combination with other herbicides, insecticides or bactericides. Especially it is essential to add one or more of agents selected from the group consisting of bentazon, Quinclorac, propanil, simetryn, 2,4-D, fenoxaprop-ethyl, linuron, MCPA, azafenidin, carfentrazone, molinate, thiobencarb, pendimethalin, bensulfuron-methyl, pyrazosulfuron-ethyl, metsulfuron-methyl, thifensulfuron-methyl, tribenuron-methyl, trifluralin, amidosulfuron, bromoxynil, butachlor, mecoprop, metribuzin, bifenox, benfuresate, isoproturon, cyhalofop-butyl, mefenaset, fentrazamide, pyriminobac-methyl, bispyribac sodium, azimsulfruon, cyclosulfamuron and pyanchor.

The herbicidal effect of the compounds of this invention was tested and the examples are as follows.

Experimental Example 1: Leaf Treatment Test

Seeds of rice, wheat, barley, corn, cotton, barnyard grass, common sorgum, large crabgrass and fall panicum were seeded at a pot with a surface area of 600 cm$^2$. When barnyard grass kept at 20~30° C. had three leaves, wettable powders prepared by mixing 1 weight part of the active compound, 5 weight part of acetone and 1 weight part of emulsifier and diluted with water was applied directly on the leaves in 2000 l per hectare. The concentration of the spray liquid was so chosen the particular amounts of the active compound desired. 14 days after the treatment, the degree of damage to the plants was rated in % damage in comparison to the development of untreated control.

| | |
|---|---|
| 0% | no action (like untreated control) |
| 20% | slight effect |
| 70% | herbicidal effect |
| 100% | total destruction |

In the test, the active compound(s) of the formula (1) according to the invention exhibited an excellent selectivity toward the plants and herbicidal activity against weeds.

The plants employed in this test are as follows.

TABLE 4

| ABRV. | SCIENTIFIC NAME | ENGLISH NAME |
|---|---|---|
| ZEAMX | *Zea mays* L. | Corn |
| GLXMA | *Glycine max* (L.) MERR | Soy bean |
| GOSHI | *Gossypium* | Cotton |
| TRZAW | *Triticum aestivum* L. | Wheat |
| ORYSA | *Oryza sativa* L. cv. *Dongjin* | Rice |
| SORBI | *Andropogon sorghum* | Common sorgum |
| ECHCG | *Echinochloa crus-galli* Beauv. var. *caudata Kitagawa* | Barnyard grass |
| DIGSA | *Digitaria Sanguinalis* (L.) SCOP | Large crabgrass |
| PANDI | *Panicum dichotomiflorum* Michx | Fall panicum |

Among the compounds of the formula (1), herbicidal activity of the compounds in table 5 is represented in the following table 6 and 7.

TABLE 5

(1)

[Chemical structure of formula (1): a chlorobenzoxazole linked via O to a phenyl group, then O-CH(CH$_3$)-C(=O)-N(R) to a fluorinated phenyl ring bearing substituents X$_n$ and Y]

| Compound No. | R | Y | X |
|---|---|---|---|
| 1 | CH$_3$ | H | H |
| 2 | CH$_2$CH$_3$ | H | H |
| 3 | CH$_3$ | H | 4,5-F$_2$ |
| 4 | CH$_3$ | F | H |
| 5 | CH$_3$ | H | 4-F |
| 6 | CH$_3$ | F | 3-F |
| 7 | CH$_3$ | H | 5-CH$_3$ |
| 8 | CH$_3$ | H | 4-Cl |
| 9 | CH$_3$ | H | 5-F |
| 10 | CH$_3$ | H | 4-CH$_3$ |
| 11 | CH$_3$ | H | 4-OCH$_3$ |
| 12 | CH$_3$ | H | 4-OCH$_2$CH$_3$ |
| control1 | H | H | H |
| control 2 (Fenoxaprop-ethyl) | | | |

TABLE 6

| | | Treated amount (kg/ha) | | |
|---|---|---|---|---|
| Active Compound | Weeds | 0.4 | 0.1 | 0.025 |
| Compound No. 1 | ZEAMX | 100 | 70 | 0 |
| | GLXMA | 20 | 0 | 0 |
| | GOSHI | 0 | 0 | 0 |
| | TRZAW | 0 | 0 | 0 |
| | ORYSA | 0 | 0 | 0 |
| | SORBI | 100 | 100 | 100 |
| | ECHCG | 100 | 100 | 90 |
| | DIGSA | 100 | 100 | 100 |
| | PANDI | 100 | 100 | 100 |
| Compound No. 2 | ZEAMX | 70 | 10 | 5 |
| | GLXMA | 10 | 0 | 0 |
| | GOSHI | 0 | 0 | 0 |
| | TRZAW | 0 | 0 | 0 |
| | ORYSA | 0 | 0 | 0 |
| | SORBI | 100 | 95 | 40 |
| | ECHCG | 95 | 80 | 20 |
| | DIGSA | 100 | 95 | 30 |
| | PANDI | 100 | 100 | 0 |
| Compound No. 3 | ZEAMX | 0 | 0 | 0 |
| | GLXMA | 10 | 0 | 0 |
| | GOSHI | 0 | 0 | 0 |
| | TRZAW | 0 | 0 | 0 |
| | ORYSA | 10 | 0 | 0 |
| | SORBI | 100 | 100 | 40 |
| | ECHCG | 95 | 60 | 0 |
| | DIGSA | 100 | 90 | 30 |
| | PANDI | 0 | 0 | 0 |
| Compound No. 4 | ZEAMX | 100 | 40 | 10 |
| | GLXMA | 20 | 0 | 0 |
| | GOSHI | 0 | 0 | 0 |
| | TRZAW | 0 | 0 | 0 |
| | ORYSA | 30 | 20 | 0 |
| | SORBI | 100 | 100 | 95 |
| | ECHCG | 100 | 95 | 80 |
| | DIGSA | 100 | 100 | 90 |
| | PANDI | 100 | 100 | 40 |

TABLE 6-continued

| Active Compound | Weeds | Treated amount (kg/ha) | | |
|---|---|---|---|---|
| | | 0.4 | 0.1 | 0.025 |
| Compound No. 5 | ZEAMX | 100 | 30 | 0 |
| | GLXMA | 0 | 0 | 0 |
| | GOSHI | 0 | 0 | 0 |
| | TRZAW | 0 | 0 | 0 |
| | ORYSA | 0 | 0 | 0 |
| | SORBI | 100 | 100 | 100 |
| | ECHCG | 100 | 100 | 0 |
| | DIGSA | 100 | 100 | 100 |
| | PANDI | 100 | 80 | 40 |
| Compound No. 6 | ZEAMX | 100 | 100 | 30 |
| | GLXMA | 0 | 0 | 0 |
| | GOSHI | 0 | 0 | 0 |
| | TRZAW | 0 | 0 | 0 |
| | ORYSA | 20 | 0 | 0 |
| | SORBI | 100 | 100 | 100 |
| | ECHCG | 100 | 100 | 95 |
| | DIGSA | 100 | 100 | 40 |
| | PANDI | 100 | 100 | 40 |
| Compound No. 7 | ZEAMX | 0 | 0 | 0 |
| | GLXMA | 10 | 0 | 0 |
| | GOSHI | 0 | 0 | 0 |
| | TRZAW | 0 | 0 | 0 |
| | ORYSA | 0 | 0 | 0 |
| | SORBI | 100 | 95 | 10 |
| | ECHCG | 40 | 40 | 20 |
| | DIGSA | 100 | 100 | 100 |
| | PANDI | 100 | 100 | 100 |
| Compound No. 8 | ZEAMX | 0 | 0 | 0 |
| | GLXMA | 0 | 0 | 0 |
| | GOSHI | 0 | 0 | 0 |
| | TRZAW | 0 | 0 | 0 |
| | ORYSA | 0 | 0 | 0 |
| | SORBI | 100 | 70 | 0 |
| | ECHCG | 70 | 0 | 0 |
| | DIGSA | 100 | 95 | 30 |
| | PANDI | 100 | 0 | 0 |
| Compound No. 9 | ZEAMX | 100 | 0 | 0 |
| | GLXMA | 0 | 0 | 0 |
| | GOSHI | 0 | 0 | 0 |
| | TRZAW | 0 | 0 | 0 |
| | ORYSA | 20 | 0 | 0 |
| | SORBI | 100 | 100 | 90 |
| | ECHCG | 80 | 80 | 70 |
| | DIGSA | 100 | 100 | 100 |
| | PANDI | 100 | 100 | 90 |
| Compound No. 10 | ZEAMX | 0 | 0 | 0 |
| | GLXMA | 0 | 0 | 0 |
| | GOSHI | 0 | 0 | 0 |
| | TRZAW | 0 | 0 | 0 |
| | ORYSA | 0 | 0 | 0 |
| | SORBI | 100 | 60 | 30 |
| | ECHCG | 80 | 0 | 0 |
| | DIGSA | 100 | 95 | 70 |
| | PANDI | 70 | 0 | 0 |
| Compound No. 11 | ZEAMX | 0 | 0 | 0 |
| | GLXMA | 0 | 0 | 0 |
| | GOSHI | 0 | 0 | 0 |
| | TRZAW | 0 | 0 | 0 |
| | ORYSA | 0 | 0 | 0 |
| | SORBI | 70 | 20 | 0 |
| | ECHCG | 40 | 0 | 0 |
| | DIGSA | 95 | 95 | 95 |
| | PANDI | 40 | 20 | — |
| Compound No. 12 | ZEAMX | 0 | 0 | 0 |
| | GLXMA | 0 | 0 | 0 |
| | GOSHI | 0 | 0 | 0 |
| | TRZAW | 0 | 0 | 0 |
| | ORYSA | 00 | 0 | 0 |
| | SORBI | 30 | 0 | 0 |
| | ECHCG | 30 | 0 | 0 |
| | DIGSA | 100 | 100 | 80 |
| | PANDI | 0 | 0 | 0 |
| control 1 | ZEAMX | 100 | 100 | 100 |
| | GLXMA | 40 | 30 | 0 |
| | GOSHJ | 0 | 0 | 0 |
| | TRZAW | 30 | 20 | 0 |
| | ORYSA | 70 | 50 | 35 |
| | SORBJ | 100 | 100 | 100 |
| | ECHCG | 100 | 100 | 100 |
| | DIGSA | 100 | 100 | 100 |
| | PANDI | 100 | 100 | 100 |
| control 1 | ZEAMX | 100 | 100 | 80 |
| | GLXMA | 30 | 0 | 0 |
| | GOSHJ | 0 | 0 | 0 |
| | TRZAW | 70 | 60 | 0 |
| | ORYSA | 90 | 70 | 40 |
| | SORBJ | 100 | 100 | 100 |
| | ECHCG | 100 | 100 | 100 |
| | DIGSA | 100 | 100 | 100 |
| | PANDI | 100 | 100 | 95 |

TABLE 7

| Active Compound | 4 Leaves | Treated amount (kg/ha) | | | |
|---|---|---|---|---|---|
| | | 1.0 | 0.25 | 0.063 | 0.016 |
| Compound No. 1 | rice | 0 | 0 | 0 | 0 |
| | Barnyard grass | 100 | 100 | 100 | 75 |
| control 2 | rice | 85 | 70 | 30 | 20 |
| | Barnyard grass | 100 | 100 | 100 | 95 |

Experimental Example 2:

Rice[*Oryza sativa. L.* cv. Chuchong(ORYSA)] and barnyard grass [*Eclzinocgloa crus-galli* beauv. var. caudate Kitagawa(ECHCG) and *Ecliinocgloa crus-galli* Beauv. var. orygicola Ohwi (ECHOR)] were planted and grown. The test compounds with 98% purity was dissolved in acetone containing tween-20 and diluted with water. Each maximum concentration of acetone and tween-20 were 25% and 0.1%.

The solution was sprayed in a proportion of 200 g a.i per hactare on the leaves. When rice{ORYSA} had 6.0~6.5 leaves with 32.8 cm of the first leaf, barnyard grass (ECHOR) had 1~2 tillering with 37.3 cm of the first leaf and barnyard grass(ECHCG) had 1~2 tillering with 44.4 cm of the first leaf.

20 and 30 days after treatment (DAT) herbicidal effect and toxicity were measured. The result is represented in the following table 8.

TABLE 8

| Active Compound | Formulation | Amount (%) | Treated amount | activity (0~100), 20 DAT ECHOR | ECHCG | toxicity (0~100) 20 DAT | 30 DAT |
|---|---|---|---|---|---|---|---|
| Compound | Tech. | 98% | 200 | 100 | 99.5 | 0 | 0 |
| control 1 | Tech. | 98% | 200 | 100 | 100 | 22 | 39 |

As a result of these tests, the compounds of the present invention exhibit an excellent selectivity toward rice and herbicidal activity against barnyard grass. And also it is proved that the compounds are very stable for the plants and useful to control weeds.

What is claimed is:

1. A herbicidal compound of the formula (1):

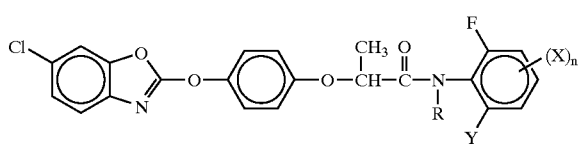

(1)

wherein,

R is a methyl group or ethyl group;

X is a hydrogen, halogen, cyano, $C_1$~$C_6$ alkyl, $C_1$~$C_6$ alkoxy, $C_1$~$C_3$ haloalkyl substituted with 1 to 3 of halogen atom(s), $C_1$~$C_3$ haloalkoxy substituted with 1 to 3 of halogen atom(s), $C_2$~$C_4$ alkoxyalkoxy, phenoxy, benzyloxy, $C_2$~$C_6$ alkenyl, $C_2$~$C_6$ alkinyl, $C_2$~$C_6$ alkenyloxy, $C_2$~$C_6$ alkinyloxy, or phenyl group;

Y is a hydrogen or a fluoro group; and n is an integer of 1 or 2, provided that when n is 2, X can be the same or different.

2. The herbicidal compound as defined in claim 1, wherein said R is $CH_3$; said X is H; said Y is H.

3. The herbicidal compound as defined in claim 1, wherein said R is $CH_3$; said X is 5-$CH_3$; said Y is H.

4. The herbicidal compound as defined in claim 1, wherein said R is $CH_3$; said X is 4,5-$F_2$; said Y is H.

5. A method of controlling barnyard grass produced while growing rice without inflicting any substantial harm to said rice which comprises applying an effective amount of at least one compound of the formula (1):

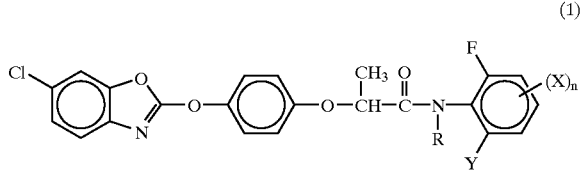

(1)

wherein,

R is a methyl group or ethyl group;

X is a hydrogen, halogen, cyano, $C_1$~$C_6$ alkyl, $C_1$~$C_6$ alkoxy, $C_1$~$C_3$ haloalkyl substituted with 1 to 3 of halogen atom(s), $C_1$~$C_3$ haloalkoxy substituted with 1 to 3 of halogen atom(s), $C_2$~$C_4$ alkoxyalkoxy, phenoxy, benzyloxy, $C_2$~$C_6$ alkenyl, $C_2$~$C_6$ alkinyl, $C_2$~$C_6$ alkenyloxy, $C_2$~$C_6$ alkinyloxy, or phenyl group;

Y is a hydrogen or fluoro group; and n is an integer of 1 or 2, provided that when n is 2, X can be the same or different.

6. The method to control barnyard grass as defined in claim 5, wherein said compound of the formula (1) is that R is $CH_3$; X is H; Y is H.

7. The method to control barnyard grass as defined in claim 5, wherein said compound of the formula (1) is that R is $CH_3$; X is 5-$CH_3$; Y is H.

8. The method to control barnyard grass as defined in claim 5, wherein said compound of the formula (1) is that R is $CH_3$; X is 4,5-$F_2$; Y is H.

9. A herbicidal composition comprising at least one compound of the formula (1) together with at least one member selected from the group consisting of: an agriculturally acceptable carrier, a supplement agent, a surfactant and at least one other herbicidal compound.

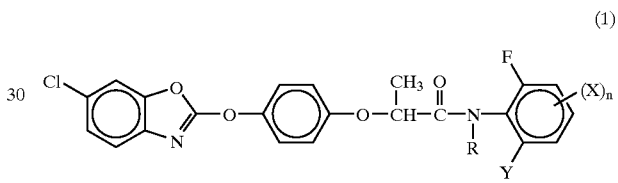

(1)

wherein,

R a methyl or ethyl group;

X is a hydrogen, halogen, cyano, $C_1$~$C_6$ alkyl, $C_1$~$C_6$ alkoxy, $C_1$~$C_3$ haloalkyl substituted with 1 to 3 of halogen atom(s), $C_1$~$C_3$ haloalkoxy substituted with 1 to 3 of halogen atom(s), $C_2$~$C_4$ alkoxyalkoxy, phenoxy, benzyloxy, $C_2$~$C_6$ alkenyl, $C_2$~$C_6$ alkinyl, $C_2$~$C_6$ alkenyloxy, $C_2$~$C_6$ alkinyloxy, or phenyl group;

Y is a hydrogen or fluoro group; and n is an integer of 1 or 2, provided that when n is 2, X can be the same or different.

10. The herbicidal composition as defined in claim 9, wherein said compound of formula (1) is that R is $CH_3$; X is H; Y is H.

11. The herbicidal composition as defined in claim 9, wherein said compound of formula (1) is that R is $CH_3$; X is 5-$CH_3$; Y is H.

12. The herbicidal composition as defined in claim 9, wherein said compound of formula (1) is that R is $CH_3$; X is 4,5-$F_2$; Y is H.

13. A method for preparing a compound of formula (1) comprising reacting a compound of the formula (6) with a compound of the formula (7):

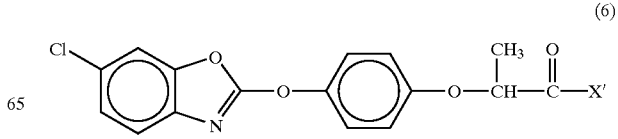

(6)

-continued

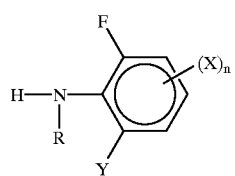
(7)

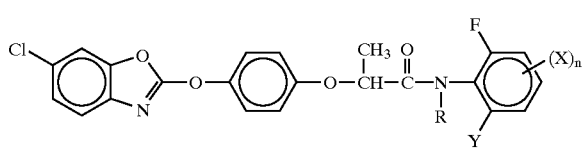
(1)

wherein,

R is a methyl or ethyl group;

X is a hydrogen, halogen, cyano, $C_1$~$C_6$ alkyl, $C_1$~$C_6$ alkoxy, $C_1$~$C_3$ haloalkyl substituted with 1 to 3 of halogen atom(s), $C_1$~$C_3$ haloalkoxy substituted with 1 to 3 of halogen atom(s), $C_2$~$C_4$ alkoxyalkoxy, phenoxy, benzyloxy, $C_2$~$C_6$ alkenyl, $C_2$~$C_6$ alkinyl, $C_2$~$C_6$ alkenyloxy, $C_2$~$C_6$ alkinyloxy, or phenyl group;

Y is a hydrogen or fluoro group;.

n is an integer of 1 or 2, provided that when n is 2, X can be the same or different; and X' is an OH, Cl, Br or phenoxy group.

14. A herbicidal compound of the formula (1):

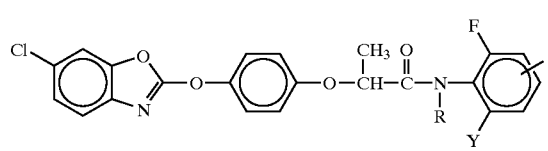
(1)

wherein,

R is $CH_3$;

X is hydrogen, fluorine, chlorine, methyl or methoxy Y is hydrogen or fluoro; and n is 1.

15. A herbicidal composition comprising at least one compound of the formula (1) together with at least one member selected from the group consisting of: an agriculturally acceptable carrier, a supplement agent, a surfactant and at least one other herbicidal compound:

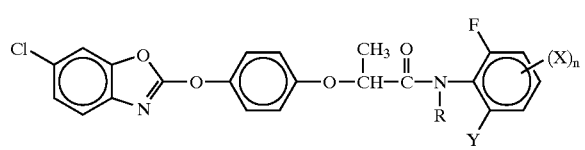
(1)

wherein,

R is a methyl group;

X is a hydrogen, fluoro, chloro, bromo, cyano, methyl, or methoxy group;

Y is hydrogen or fluoro; and n is 1.

16. A method for preparing a compound of formula (1) comprising reacting a compound of the formula (6) with a compound of the formula (7):

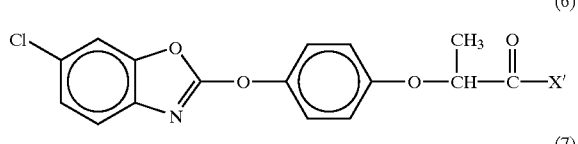
(6)

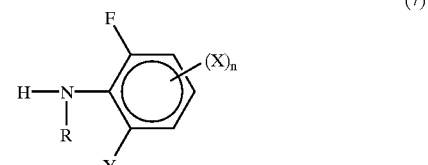
(7)

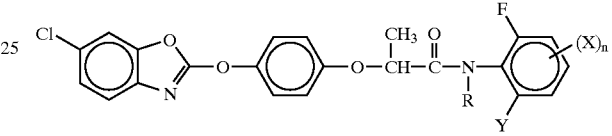
(1)

wherein,

R is a methyl group;

X is a hydrogen, fluoro, chloro, bromo, cyano, methyl, or methoxy group;

Y is hydrogen or fluoro;

n is 1; and

X' is OH, Cl, Br or phenoxy group.

17. A method of controlling barnyard grass produced while growing rice without inflicting any substantial harm to said rice which comprises applying an effective amount of at least one compound of the formula (1):

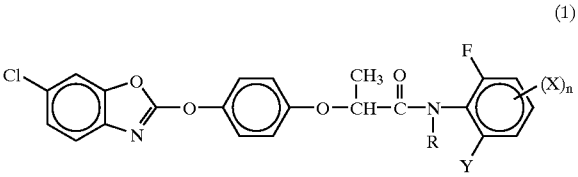
(1)

wherein,

R is a methyl group;

X is a hydrogen, fluoro, chloro, bromo, cyano, methyl or methoxy group;

Y is a hydrogen or fluoro group; and n is 1.

* * * * *